United States Patent [19]
Fladd et al.

[11] Patent Number: 5,764,345
[45] Date of Patent: Jun. 9, 1998

[54] METHODS FOR DETECTING INHOMOGENEITIES, SPECIFICALLY, STRIAE, INFUSED SILICA GLASSES

[75] Inventors: David R. Fladd, Canton; Stephen J. Rieks, Moravia, both of N.Y.

[73] Assignee: Corning Incorporated, Corning, N.Y.

[21] Appl. No.: 710,093

[22] Filed: Sep. 11, 1996

Related U.S. Application Data

[60] Provisional application No. 60/003,607 Sep. 12, 1995.

[51] Int. Cl.⁶ .............. G01L 1/24; G01B 11/00; G06G 7/12
[52] U.S. Cl. .......... 356/35.5; 356/359; 364/572; 364/575
[58] Field of Search .............. 356/35.5, 359–360, 356/345; 364/570–572, 573, 575

[56] References Cited

U.S. PATENT DOCUMENTS

| | | | |
|---|---|---|---|
| 4,195,931 | 4/1980 | Hara | 356/346 |
| 4,998,017 | 3/1991 | Ryan et al. | 356/352 |
| 5,133,601 | 7/1992 | Cohen et al. | 356/359 |
| 5,416,586 | 5/1995 | Tronolone et al. | 356/359 |
| 5,479,006 | 12/1995 | Schultz | 250/559.37 |
| 5,544,518 | 8/1996 | Hart et al. | 364/571.02 |

FOREIGN PATENT DOCUMENTS 6-308717 of 1994 Japan.

OTHER PUBLICATIONS

"Corning Tests for Striae in Fused Silica," *Laser Focus World*, p. 110, Aug. 1993.
Pfau et al., *Applied Optics*, vol. 31, No. 31, pp. 6658–6661 (Nov. 1, 1992).

*Primary Examiner*—Frank G. Font
*Assistant Examiner*—Jason D. Vierra-Eisenberg
*Attorney, Agent, or Firm*—Maurice M. Klee

[57] ABSTRACT

A process for detecting inhomogeneities, specifically, striae in a sample of fused silica glass is provided which includes the steps of: preparing a digitized phase plot for the sample using an interferometer which produces a beam of light which passes through the sample; applying a high pass filter to the phase plot to remove the effects of the sample's bulk properties; applying a statistical filter to the high pass filtered data to remove outlying data points; and column averaging the statistically filtered data. If present, striae can be readily detected in the column averaged, statistically filtered data.

17 Claims, 6 Drawing Sheets

| 50 | 111 | 21 | 46 | 199 | 140 | 54 | 87 | 111 |
|---|---|---|---|---|---|---|---|---|
| 57 | 121 | 31 | 53 | 198 | 137 | 55 | 88 | 114 |
| 63 | 116 | 24 | 49 | 214 | 146 | 49 | 94 | 118 |
| 55 | 102 | 33 | 35 | 218 | 139 | 57 | 88 | 121 |
| 71 | 92 | 18 | 44 | 197 | 137 | 54 | 91 | 119 |
| 66 | 114 | 23 | 48 | 197 | 145 | 52 | 90 | 113 |
| 65 | 108 | 27 | 53 | 214 | 142 | 51 | 92 | 117 |

2 DIMENSIONAL ARRAY
OF RESIDUAL DATA FILE

| 61 | 109 | 25 | 47 | 205 | 141 | 53 | 90 | 116 |
|---|---|---|---|---|---|---|---|---|

AVERAGE OF THE DATA COLUMNS

| 61 | 109 | 25 | 47 | 205 | 141 | 53 | 90 | 116 |
|---|---|---|---|---|---|---|---|---|
| 61 | 109 | 25 | 47 | 205 | 141 | 53 | 90 | 116 |
| 61 | 109 | 25 | 47 | 205 | 141 | 53 | 90 | 116 |
| 61 | 109 | 25 | 47 | 205 | 141 | 53 | 90 | 116 |
| 61 | 109 | 25 | 47 | 205 | 141 | 53 | 90 | 116 |
| 61 | 109 | 25 | 47 | 205 | 141 | 53 | 90 | 116 |
| 61 | 109 | 25 | 47 | 205 | 141 | 53 | 90 | 116 |

STRIAE ARRAY

FIG. 9

METHODS FOR DETECTING INHOMOGENEITIES, SPECIFICALLY, STRIAE, INFUSED SILICA GLASSES

CROSS REFERENCE TO RELATED PROVISIONAL APPLICATION

This application claims the benefit under 35 USC §119(e) of U.S. Provisional application Ser. No. 60/003,607 filed Sep. 12, 1995.

FIELD OF THE INVENTION

This invention relates to methods for detecting and quantifying inhomogeneities in the index of refraction of fused silica glasses using interferometric techniques. In particular, the invention relates to detecting and quantifying striae in such glasses.

DESCRIPTION OF THE TECHNOLOGY

Fused silica glasses of high homogeneity can be made by a variety of processes, one of the most common of which involves depositing $SiO_2$ soot particles on the hot surface of a rotating body (often referred to as a "boule"). In the art, glass making procedures of this type are known as vapor phase hydrolysis/oxidation processes or simply as flame hydrolysis processes.

As practiced commercially, boules can have diameters on the order of five feet (1.5 meters) and thicknesses on the order of 5–8 inches (13–20 cm). Multiple blanks are cut from such boules and used to make various products, including optical elements, such as, lenses (including lenses for microlithography systems), prisms, and the like.

The blanks are generally cut in a direction parallel to the axis about which the boule was rotated during its formation. The optical axis of a lens element made from such a blank will also generally be parallel to the boule's axis of rotation. For ease of reference, measurements of inhomogeneity made in this direction will be referred to herein as "z-axis" or "z-direction" measurements. Measurements made in a direction perpendicular to the z-axis will be referred to as "off-axis" measurements. The present invention is primarily concerned with off-axis inhomogeneity measurements.

Boules produced by a flame hydrolysis process often exhibit small variations in the index of refraction of the glass as one moves along the z-axis. These variations tend to be constant in planes orthogonal to the z-axis. It is these planes which give rise to the off-axis striae which the present invention is designed to detect and quantify. For ease of reference, the planes will be referred to herein as "striae planes". In some cases, the planes repeat in a regular periodic pattern. Such striae are referred to herein as "off-axis periodic striae" or simply "periodic striae".

The amount of variation in the index of refraction of a blank which can be tolerated depends on the product which is to be made from the blank. For example, extremely high levels of z-axis and off-axis homogeneity are required for the optical elements employed in microlithography systems which are used to produce integrated circuits. See, for example, Pfau et al., "Quartz inhomogeneity effects in diffraction-limited deep ultraviolet imaging," *Applied Optics*, Vol. 31, No. 31, pages 6658–6661 (Nov. 1, 1992) and Japanese Patent Application Disclosure No. 6-308717, published Nov. 4, 1994.

Various approaches have been considered for determining whether a blank or optical element meets the homogeneity requirements of particular applications. For example, off-axis homogeneity can be observed and/or measured through the use of a shadowgram in which diverging light from a point source is passed through a sample and the resulting pattern is observed on an observation screen. Similarly, diffraction-based techniques can be used where collimated light is passed through a sample and the far-field diffraction pattern is observed in the Fourier transform plane of a long focal length lens. See "Corning Tests for Striae in Fused Silica," *Laser Focus World*, page 110, August 1993.

Perhaps the most commonly used approach is to test the blanks or optical elements with an interferometer. The present invention is concerned with such interferometric testing.

FIG. 1 is a schematic diagram illustrating suitable equipment for measuring the off-axis homogeneity of a sample 13 of fused silica glass. It is to be understood of course that the system shown in FIG. 1 is for purposes of illustration only and is not intended to limit the scope of the invention. Other types of interferometers employing different components and having different layouts can be used in the practice of the invention if desired.

In the system of FIG. 1, interferometer mainframe 15 (e.g., a ZYGO brand mainframe, Zygo Corporation, Middlefield, Conn.) produces a collimated beam of laser light 17 which passes through phase modulation unit 19, oil-on plate 23, sample 13, and oil-on plate 25. The beam then strikes reference flat 27 and is reflected back to mainframe 15 through the same components. The system of FIG. 1 also includes beam reducer 21, the use of which constitutes one of the aspects of the invention and is discussed below.

Phase modulation unit 19 is controlled by mainframe 15 and serves to vary the optical path length between the mainframe and the reference flat as the interference pattern is generated. Oil-on plates 23 and 25 provide substantially flat air-glass interfaces for sample 13 without the need for extensive polishing of the sample.

Sample 13 is mounted on a swivel table, shown schematically by reference numbers 29, which allows the sample to be rotated relative to beam 17 in order to optimize the intensity of the interference pattern produced by off-axis striae. If desired, the swivel table can be motorized. In practice, it has been found that the interference pattern is highly sensitive to the angle between the striae planes and beam 17. In particular, for off-axis periodic striae having a spatial period $\Delta z_{striae}$, the angular range over which the interference pattern generated by the striae can be observed can be shown to be theoretically given by:

$$\theta = \pm \arctan (\Delta z_{striae}/PL) \qquad (1)$$

where PL is the pathlength through the sample.

The angle $\theta$ is generally less than a degree for the periodic striae encountered in practice and typical pathlengths. Moreover, in actual practice, the useable angular range has been found to be even smaller than that predicted by equation (1). Accordingly, detection of striae depends on careful alignment of sample 13 with beam 17.

The interference pattern produced by a sample can be displayed as, for example, a fringe pattern or a phase plot. As discussed fully below, the present invention detects striae by analysis of phase plots, as opposed to fringe patterns. Mainframe 15 includes (or is associated with) a digital camera for recording and displaying such plots. To be useful in the practice of the present invention, the interferometer/camera system must have a sufficiently fine spatial resolution to detect the inhomogeneities of interest.

For example, the spatial resolution is preferably in the range of 18–20 pixels/mm of glass for periodic off-axis striae having $\Delta z_{striae}$ values in the 0.5 to 3.0 mm range. Such resolution can be achieved by employing a high resolution camera. Alternatively, as discussed in detail below, this level of resolution can be achieved through the use of beam reducer 21. Higher levels of resolution can, of course, be used if desired. Similarly, lower resolutions can be used for striae having a larger spatial extent or if the loss of information resulting from such lower resolution can be tolerated.

Historically, striae have been characterized by visual observation of interferometric fringes. According to this method, striae are defined as kinks or abrupt ripples in otherwise continuous fringes. The fringes may be straight or slightly curved, with the magnitude of the fringe curves being much greater than the magnitude of the fringe kinks caused by striae.

Specifications have been placed on off-axis striae in terms of a comparison between the observed interferometric fringes for a sample and those of limit samples. FIG. 2 illustrates this approach, where FIGS. 2A and 2B show target and low limit fringe patterns, respectively, and FIGS. 2C and 2D show reject and pass samples, respectively.

The subjective nature of this limit sample approach is evident from FIG. 2. The present invention is directed at providing an improved method for detecting and quantifying striae which is not subject to the subjective limitations of the prior art.

SUMMARY OF THE INVENTION

In view of the foregoing, it is an object of this invention to provide improved methods for detecting and quantifying striae in transparent bodies, such as bodies composed of fused silica. It is a further object of the invention to provide striae detection and quantification methods which can be used in the manufacturing of transparent bodies, specifically, in the quality control procedures used to determine if the bodies have an adequate level of index of refraction homogeneity for particular applications.

To achieve these and other objects, the invention in accordance with certain of its embodiments provides a process for detecting striae in a sample comprising the steps of:

(1) preparing a digitized phase plot for the sample using an interferometer, said digitized phase plot comprising a set of first values at a set of first locations on the sample;

(2) applying a high pass filter to the set of first values to remove the effects of the sample's bulk index of refraction properties, said high pass filtering producing a set of second values at a set of second locations on the sample;

(3) applying a statistical filter to the set of second values to removes outlying data points, said statistical filtering producing a set of third values at a set of third locations on the sample;

(4) column averaging the set of third values to produce a set of fourth values at the set of second locations on the sample; and (5) examining (e.g., analyzing) the set of fourth values at the set of second locations to detect striae.

In certain preferred embodiments of the invention, the high pass filtering (step 2) is performed by applying a low pass filter to the set of first values to provide a filtered set of first values and then subtracting the filtered set of first values from the original set of first values to produce the set of second values. The low pass filtering is preferably performed by local averaging, although other methods can be used if desired.

Depending upon the type of high pass filtering performed, the set of second locations on the sample can be identical to the set of first locations or can be a subset thereof. In the preferred embodiments of the invention, where the high pass filtering involves local averaging, the set of second locations is a subset of the set of first locations, i.e., it comprises the set of first locations minus data points along the edges of the set of first locations.

The statistical filtering step (step 3) is optional and can be omitted if desired.

Depending upon the statistical filter used, the set of third locations can be identical to the set of second locations or a subset thereof. For example, if outlying data points are simply eliminated (the preferred approach), the set of third locations will be a subset of the set of second locations. On the other hand, if outlying values are replaced with substitute values, the set of third locations will be identical to the set of second locations.

By means of the column averaging step (step 4), the striae become dramatically apparent, as can be seen by comparing FIG. 10 with any of FIGS. 3, 5, 6, or 8. As illustrated in FIG. 11, the column averaged set of values can be used to set objective, as opposed to subjective, quality control standards for straie in transparent media.

Figure 3:
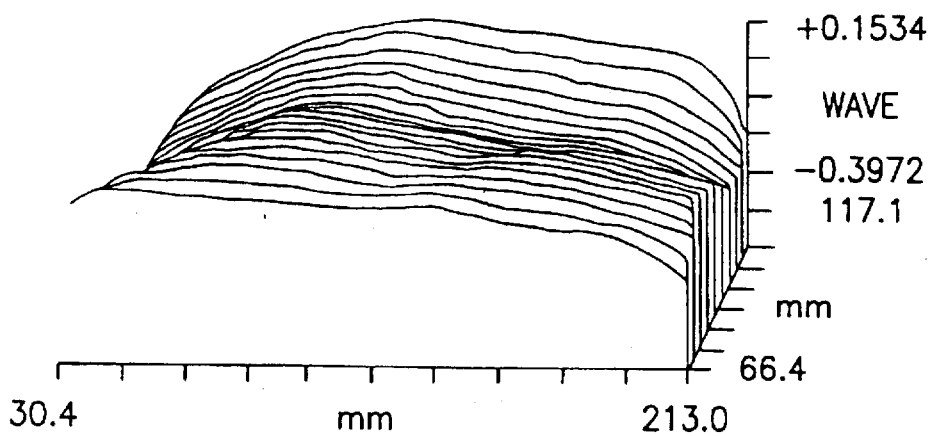
FIG. 3 is an off-axis interferometric phase plot for a fused silica blank. The "wave" parameter used in this figure and in FIGS. 5–8 and 10 represents the phase of the wavefront in terms of the wavelength of the interferometer's laser. A typical value for the wavelength is 632.8 nm.

The values shown in FIG. 3 have been preprocessed to remove contributions of piston (PST) and tilt (TLT), as is conventional for phase plots of bulk materials. Cavity errors, including errors from the oil-on plates, have not been removed from the values of this plot since, as discussed above, the sample generally needs to be rotated so that the striae can be observed. Such rotation, among other things, causes beam 17 to strike the oil-on plates at different locations thus, in effect, changing the cavity as the striae are observed. Cavity errors, however, are generally of low frequency and thus are removed during the high pass filtering step of the invention. Moreover, cavity errors tend to be minimized when a beam reducer is used as a result of the reduction in beam size.

Figure 4:
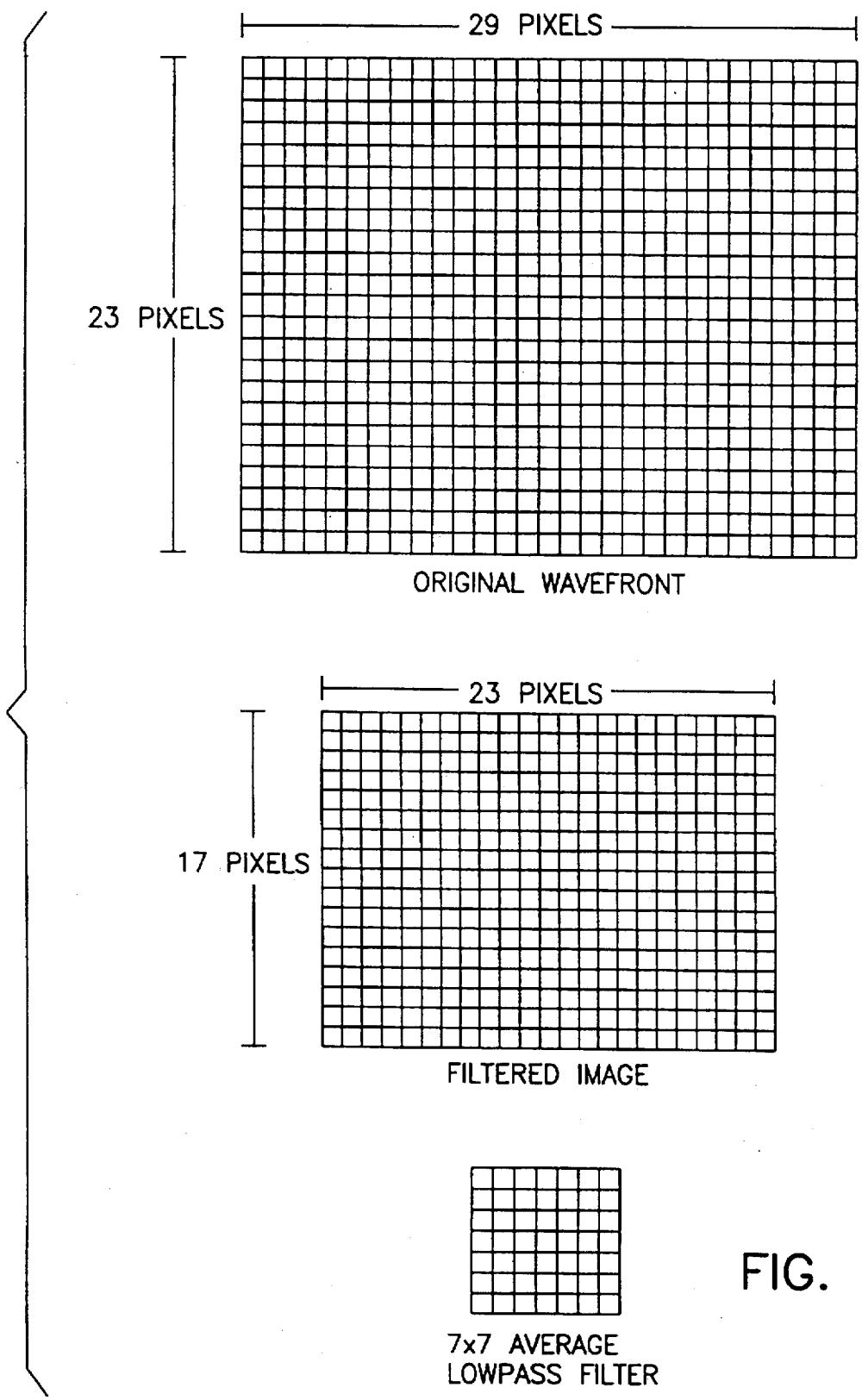

FIG. 4 is a schematic diagram illustrating a preferred procedure for performing low pass filtering on an interferometric phase plot.

Figure 5:
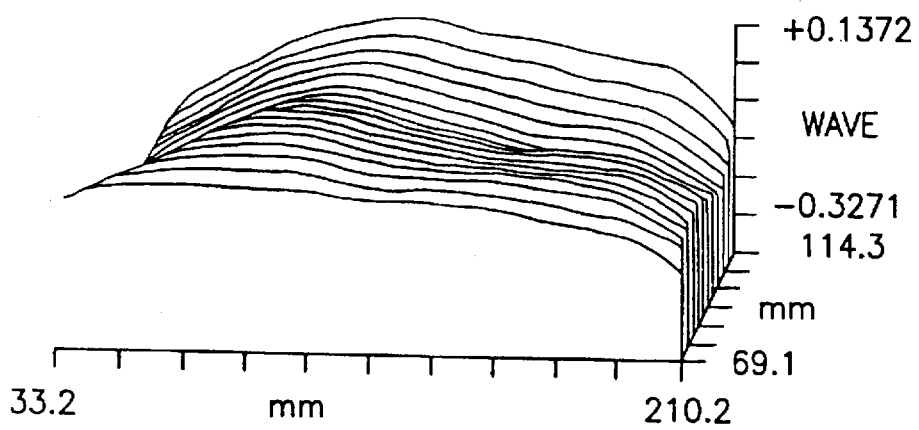

FIG. 5 is a plot of the results of applying the preferred low pass filtering procedure illustrated in FIG. 4 to the plot of FIG. 3.

Figure 6:
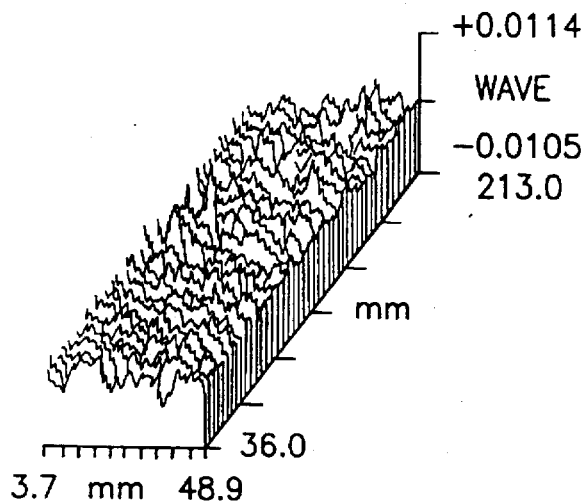

FIG. 6 is a plot of the difference between the plots of FIG. 3 and FIG. 5. FIG. 6 thus constitutes a high pass filtered version of the data of FIG. 3.

Figure 7:
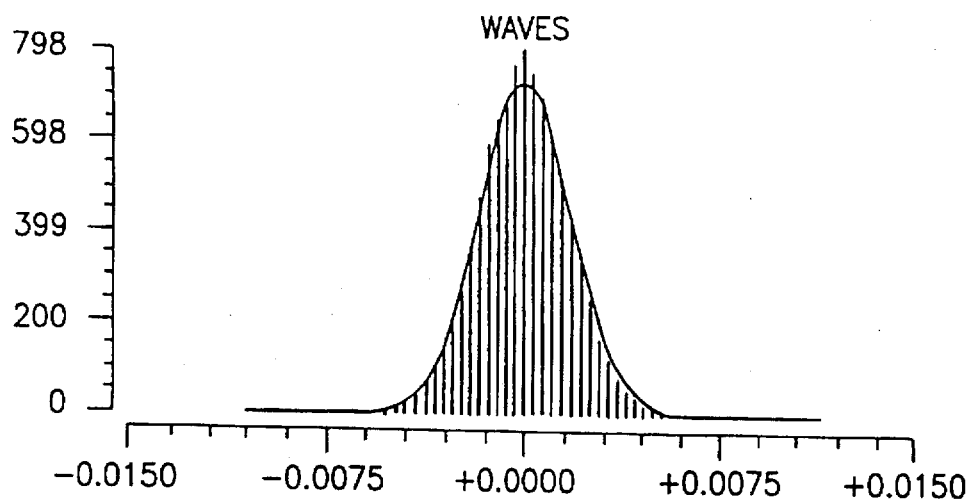

FIG. 7 is a histogram of the data values of FIG. 6.

Figure 8:
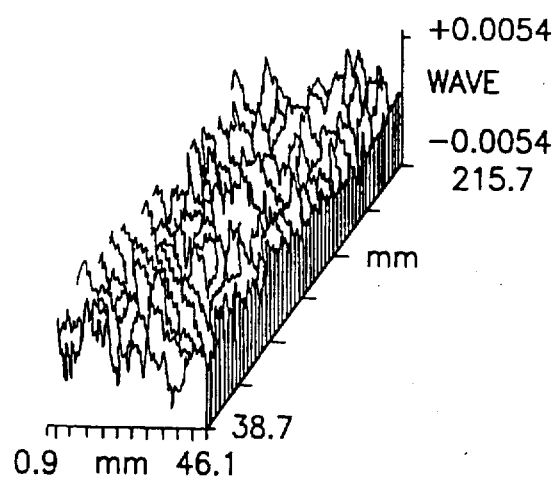

FIG. 8 shows the results of statistical filtering of the plot of FIG. 6 based on the statistical distribution of the high pass filtered data as shown in FIG. 7.

FIG. 9 is a schematic diagram illustrating the column averaging step of the invention.

Figure 10:
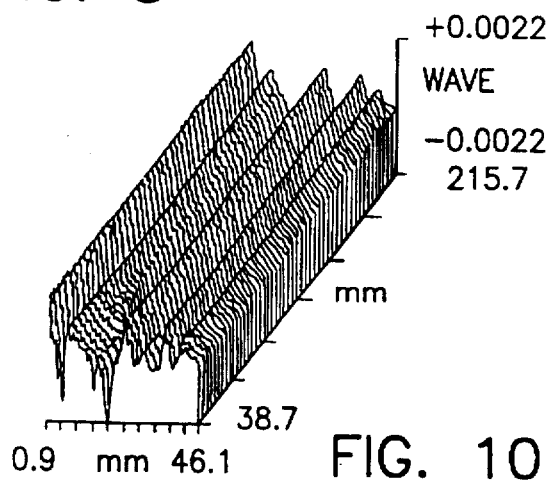

FIG. 10 shows the results of applying the column averaging step to the plot of FIG. 8.

Figure 11:
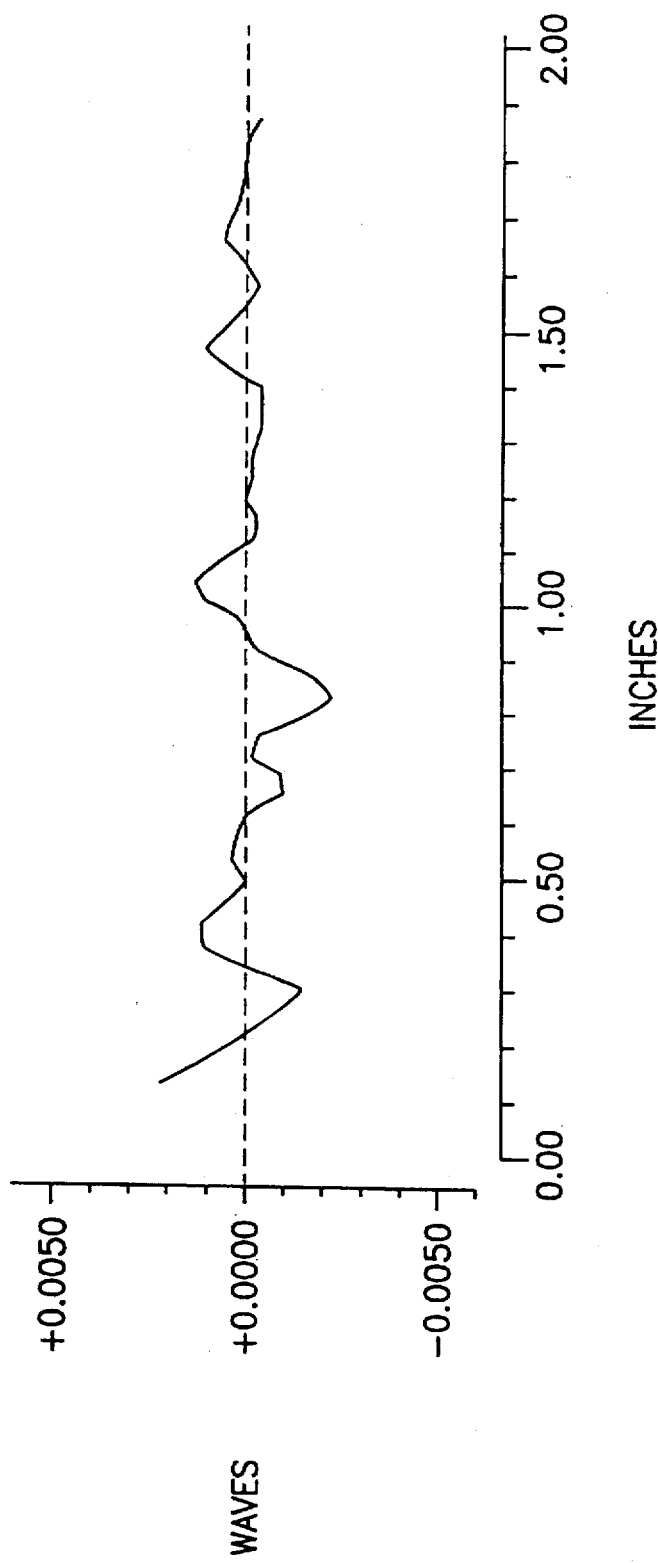

FIG. 11 is a profile line for the plot of FIG. 10 which can be used to set quality control standards for permissible levels of striae.

The foregoing drawings, which are incorporated in and constitute part of the specification, illustrate the preferred embodiments of the invention, and together with the description, serve to explain the principles of the invention. It is to be understood, of course, that both the drawings and the description are explanatory only and are not restrictive of the invention.

DESCRIPTION OF THE PREFERRED EMBODIMENTS

As discussed above, the present invention relates to methods for detecting and quantifying striae in transparent bodies such as blanks or optical elements (collectively, samples) of fused silica glass. The first step of the process comprises preparing a digitized phase plot for the sample using an interferometer, i.e., the first step comprises obtaining a set of first measured values (phase values) at a set of first locations on the sample.

In order to properly resolve an image detail, the spatial resolution at the digital camera of the interferometer system must be greater than the size of the image detail. For example, to properly resolve a defect which is 1 mm in size, the camera resolution should be at least about 10 pixels/mm, where "pixels/mm" means camera pixels/millimeter-on-the-test-piece. Accordingly, to resolve a 1 mm defect, there should be at least 10 measurement points across the size of the defect. Higher resolutions (>10 pixels/mm), of course, will result in a better representation of the actual defect, and lower resolutions (<10 pixels/mm) will result in a poorer representation. If the resolution drops below 1 pixel/mm, defects smaller than a millimeter will not be seen at all.

Figure 1:
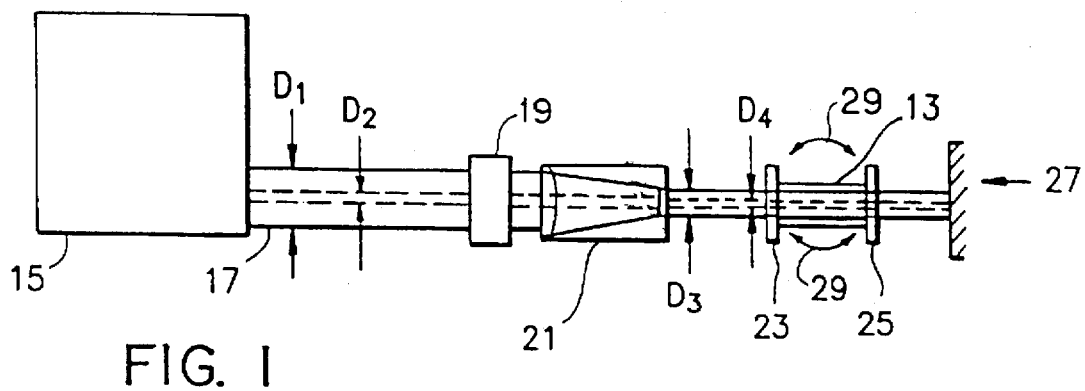
FIG. 1 is a schematic diagram of an interferometer system suitable for use in practicing the present invention. The drawing is not intended to indicate scale or relative proportions of the elements shown therein.
Figure 2A:
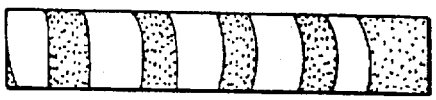
FIG. 2a–d illustrate a prior art technique for detecting striae and providing quality control standards for fused silica products wherein a fringe pattern for a sample is compared with fringe patterns for limit samples.
Figure 2B:
Figure 2C:
Figure 2D:

The striae observed in fused silica blanks can have characteristic dimensions as small as 0.5 mm. Accordingly, as indicated above, it is preferred that the interferometer/camera system have a resolution of 18–20 pixels/mm. This can be achieved through the use of a high resolution camera. Alternatively, as shown in FIG. 1, a beam reducer 21 can be used for this purpose.

The beam reducer allows beam 17 to be focused down onto a small portion of the sample as the beam passes from the mainframe to the reference flat and to be expanded back out to its original diameter as it passes back through the system. In this way, a high spatial resolution can be achieved at the camera.

For example, a typical interferometer camera can have 210 pixels in the x-direction and 230 pixels in the y-direction. A typical diameter $D_1$ for beam 17 is 100 mm. Accordingly, the spatial resolution at the camera is approximately 2 pixels/mm if no adjustments are made to the beam.

Interferometers typically have some zoom (magnification) capability, a typical maximum value being 6×. When run at this maximum magnification, the effective aperture $D_2$ of the system can be reduced to around 17 mm, giving a spatial resolution at the camera of around 12 pixels/mm. Although better than 2 pixels/mm, this level of resolution is generally not high enough to resolve off-axis inhomogeneities and, in particular, off-axis periodic striae.

Beam reducer 21 solves this problem by operating on $D_1$ so that it becomes $D_3$ which, when operated on by the interferometer's zoom system, gives an effective aperture $D_4$. For a 3:1 beam reducer and a 100 mm beam, the desired spatial resolution of 18–20 pixels/mm can be readily achieved with the interferometer's zoom system operating at a magnification in the 3× range.

The beam reducer has the advantage of being a relatively inexpensive way of achieving a high level of resolution. However, since the size of the beam is reduced, only a small portion of the sample can be examined at any one time. Such a reduction in sampling size does, however, have some advantages. As discussed above, cavity errors tend to be small when a beam reducer is used. Also, the low spatial frequency components of the phase plot tend to be relatively constant for small sampling sizes which allows the high pass filtering, as well as the statistical filtering, to be eliminated in some cases. When such a modification is made, the column averaging step still provides the important advantages of making the striae dramatically apparent and allowing the sample to be tested objectively, as opposed to subjectively, for striae.

Once a phase plot of suitable resolution has been obtained, the next step in the process involves high pass filtering of that plot so that striae can be distinguished from bulk refractive index variations. Various approaches can be used to filter out the low frequency variation in the phase plot, examples of which can be found in textbooks on digital filtering. A preferred approach involves applying a low-pass, average filter to the phase plot data and then subtracting the resulting low frequency data from the original data to obtain the desired high frequency data.

The low pass filter can take the form of a square array of pixels (a sub-array) which is translated across the original data, with the center pixel at each point being replaced with the average of the pixels within the sub-array. Put another way, in accordance with this approach, for each pixel in the image, a kernel of given size surrounding the pixel is used to compute the mean of all surrounding pixels and the value so computed is placed in the location of the pixel of interest. The process is repeated for every pixel. FIG. 4 schematically illustrates this approach.

The size of the kernel (sub-array) should be chosen to be a good fit to the general contour of the phase plot while smoothing over the striae. In practice, a subarray which corresponds to a 7 mm×7 mm area on the glass sample has been found to work successfully for fused silica glasses. Other sub-array sizes can, of course, be used if desired. It should be noted that the 7×7 sub-array in FIG. 4 is for purposes of illustration only. The actual size of the sub-array to achieve a 7 mm ×7 mm area will depend on the resolution of the interferometer/camera system. If that resolution is 1 pixel/mm, a 7×7 sub-array will correspond to a 7 mm×7 mm area on the glass sample.

A disadvantage of the local averaging approach is that data are lost around the edges of the image, where the kernel is not complete. This is illustrated in FIG. 4 by the reduction from 29×23 pixels to 23×17 pixels, three pixels being lost along each of the four edges of the original data array. The information in these lost pixels is, however, used in the calculation of the outmost pixels that remain.

An alternate to the above approach is to utilize a two-dimensional fit to the raw data. A common polynomial used to fit phase plot data is the Zernike polynomial and commercially available interferometers, including ZYGO brand interferometers, typically include software for performing high pass filtering using this polynomial.

The Zernike polynomial normally has 36 terms, which closely resemble the classic Seidel aberrations such as focus, coma, stigmatism, etc. A subset of Zernike terms, e.g., PST (piston), TLT (tilt), PWR (power), AST (astigmatism), and CMA (coma) in the ZYGO nomenclature, will generally fit the low frequency components of the raw data quite well. If this fit is then subtracted from the raw data, the desired high frequency data is obtained.

In comparison to the filtering by the local averaging approach, the Zernike polynomial approach has the advantage that no data are lost around the edge. Its disadvantages are that one needs a circular dataset and the fit is optimized for circularly-symmetric errors. Because most striae files are rectangular, the local averaging approach is, in general, preferred.

The local averaging approach is also preferred because it can be applied more than once to first detect relatively large striae and subsequently detect striae having a smaller spatial extent. Thus, the raw data can be processed with a relatively large kernel, corresponding to a relatively large area on the sample, to remove bulk effects while leaving both large and small striae in the high pass data, and then the high pass data can be reprocessed with a smaller kernel which removes large striae but leaves small striae to produce a new set of high pass data specifically directed to the small striae. The kernel sizes are picked based on the expected dimensions of the striae and the resolution of the interferometer/camera system which, as discussed above, determines the area on the sample to which a pixel corresponds.

Whatever filtering technique is used, the result is a set of data values containing only the high frequency information in the original phase plot. FIGS. 3, 5, and 6 illustrate the transformation from raw data to high frequency data by means of the low pass, averaging filter. Specifically, FIG. 3 shows the raw data, FIG. 5 the raw data after low pass filtering, and FIG. 6 the difference between the raw data and the low pass filtered data. Note that the axes in FIG. 6 have been rotated 90 degrees counter-clockwise relative to those of FIGS. 3 and 5 to make the striae more visible on the isometric plot. Even with this rotation, the striae are difficult to see in FIG. 6.

The high frequency data includes the effects of striae, as well as other random, noisy information, usually consisting of spikes. Some spikes may be due to dust on lenses, retroreflections, or unknown causes.

As discussed above, for a flame hydrolysis process, off-axis striae in fused silica can be essentially planar with the peaks and valleys of the striae occurring in essentially a parallel orientation in the phase plot. In terms of imaging, the peaks and valleys of the striae can be made to occur along the rows or columns of the image, depending on the orientation of the sample. To separate the striae planes from random noise, two further processing steps are performed, namely, statistical filtering and column averaging.

Statistical filtering serves to remove spurious high frequency effects from the data, while enhancing the striae. When a histogram of pixel values from the high frequency data is plotted, the graph closely resembles a normal curve, with the center of the curve being the average pixel value for the data. See FIG. 7.

For a perfect normal curve, the average plus or minus three standard deviations (av. $\pm 3\sigma$) represents 99.7% of all data points. If we consider that spurious data usually consists of spikes, which may be either high or low points in the data, then removal of 0.3% of the highest and lowest data should enhance the striae.

The statistical filter ("sigma filter") works in this way and is used to eliminate those data points which fall outside the $\pm 3\sigma$ range. Specifically, in accordance with this aspect of the invention, the mean and standard deviation of the high frequency data is determined and those points which lie outside of the $\pm 3\sigma$ range are marked as "no data" points. It is this marking of "no data" points which produces the set of third locations on the sample discussed above. Alternatively, the outlying values at these points can be replaced with a substitute value such as a local mean or the global mean for the entire data set. In this case, the set of third locations is identical to the set of second locations.

FIG. 8 represents the results of applying this procedure (specifically, the "no data" point procedure) to the high frequency data of FIG. 6. A comparison of these two plots shows the enhancement of the striae component achieved by the statistical filtering.

The column averaging step further eliminates the random noise based on the fact that the striae occur in planes and that the planes are oriented along the pixel matrix of the image. Each column (or row) of pixels which lies parallel to the striae planes has its mean of pixel values calculated. As schematically illustrated in FIG. 9, the result is a line of data, with each value representing the mean of pixel values along the entire column. A new image is then constructed which consists of the column averaged profile line in place of the high frequency data. That is, as illustrated in FIG. 9, the column average value is substituted for each pixel in the column. It should be noted that this substitution is done for every pixel in the high pass data set, irrespective of whether some of those pixels were designated as "no data" points in the statistical filtering step. Accordingly, after the column averaging step, data exists for the entire set of second locations.

FIG. 10 shows the result the column averaging step. As this figure demonstrates, the striae are now clearly evident.

FIG. 11 illustrates how the column averaged data can be used to quantify striae in an objective manner. This figure constitutes a line plot of the column averaged data. Various criteria can be applied to this line plot to establish quality control criteria for acceptable levels of striae.

For example, local maxima and minima can be identified and described by their amplitude in terms of waves (y-axis) and their location in mm (x-axis). The magnitude of striae can then be defined by the optical path difference between adjacent local maxima and minima (waves per striae) or by the lateral distance between local maxima and minima (mm). Alternatively, both of these variables can be used to specify a wavefront slope per striae (waves per striae per mm).

Specifically, off-axis striae, including, in particular, periodic off-axis striae, can be characterized by a $\Delta n_{striae}/\Delta z_{striae}$ value, where $\Delta n_{striae}$ is the average peak-to-valley magnitude of the striae's index of refraction variation and $\Delta z_{striae}$ is the average peak-to-peak period of that variation determined from a profile line like that of FIG. 11. A variation expressed in waves can, of course, be readily transformed into one expressed in terms of index of refraction by multiplying by the interferometer's wavelength (e.g., 632.8 nm) and dividing by the thickness of the sample.

Other criteria, of course, can be used if desired. Whatever criterium or collection of criterium is chosen, the quantification step can be readily automated and the results compared to quality control value or values to reject or accept particular samples.

Although specific embodiments of the invention have been described and illustrated, it is to be understood that modifications can be made without departing from the invention's spirit and scope. For example, although the invention has been primarily described in terms of fused silica glasses made by a flame hydrolysis process, it can be used with fused silica glasses made by other processes. Similarly, the invention can be used to detect striae in transparent materials other than fused silica glasses.

A variety of other modifications which do not depart from the scope and spirit of the invention will be evident to persons of ordinary skill in the art from the disclosure herein. The following claims are intended to cover the specific embodiments set forth herein as well as such modifications, variations, and equivalents.

What is claimed is:

1. A method for testing a transparent body for the presence of striae comprising the steps of:
   (a) preparing a digitized phase plot for the transparent body using an interferometer, wherein:
      (i) the interferometer produces a beam of light which passes through the transparent body; and
      (ii) the digitized phase plot comprises a set of first values at a set of first locations on the body;
   (b) applying a high pass filter to the set of first values, said high pass filter producing a set of second values at a set of second locations on the body;
   (c) applying a statistical filter to the set of second values to remove outlying values, said statistical filter producing a set of third values at a set of third locations on the body;
   (d) column averaging the set of third values to produce a set of fourth values at the set of second locations on the body; and
   (e) examining the set of fourth values at the set of second locations to detect striae within the transparent body.

2. The method of claim 1 wherein step (b) is performed by:
   (i) low pass filtering the set of first values to produce a set of low pass filtered values at the set of second locations; and
   (ii) subtracting the set of low pass filtered values from the set of first values to produce the set of second values at the set of second locations.

3. The method of claim 2 wherein the low pass filtering comprises local average filtering of the set of first values.

4. The method of claim 3 wherein the set of second locations comprises the set of first locations minus locations along the outer edges of the set of first locations.

5. The method of claim 2 wherein the low pass filtering comprises fitting a Zernike polynomial to the set of first values.

6. The method of claim 5 wherein the set of first locations and the set of second locations are the same.

7. The method of claim 1 wherein the set of third locations is a subset of the set of second locations.

8. The method of claim 1 wherein the set of third locations is identical to the set of second locations.

9. The method of claim 1 wherein step (e) comprises applying a quality control criterium to the set of fourth values.

10. The method of claim 9 wherein the set of fourth values is transformed into a line profile before the quality control criterium is applied.

11. The method of claim 1 wherein the interferometer includes a beam reducer.

12. The method of claim 1 wherein the transparent body is composed of fused silica.

13. A method for testing a transparent body for the presence of striae comprising the steps of:
   (a) preparing a digitized phase plot for the body using an interferometer which produces a beam of light which passes through the transparent body;
   (b) column averaging the digitized phase plot; and
   (e) examining the column averaged phase plot to detect striae within the transparent body.

14. The method of claim 13 including the additional step between steps (a) and (b) of applying a high pass filter to the phase plot.

15. The method of claim 13 including the additional steps between steps (a) and (b) of:
   (i) applying a high pass filter to the phase plot; and
   (ii) applying a statistical filter to the results of the high pass filter to remove statistical outliers.

16. The method of claim 13 wherein the interferometer includes a beam reducer.

17. The method of claim 13 wherein the transparent body is composed of fused silica.

* * * * *